(12) United States Patent
Ju et al.

(10) Patent No.: US 10,111,735 B2
(45) Date of Patent: *Oct. 30, 2018

(54) DOUBLE-CUSHIONED DENTAL IMPLANT

(71) Applicant: JTI BIOMED CORP., Tainan (TW)

(72) Inventors: Chien-Ping Ju, Kansas City, MO (US); Jiin-Huey Chern Lin, Winnetka, IL (US); Yen-Chun Chen, Kaohsiung (TW)

(73) Assignee: JTI BIOMED CORP., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/818,054

(22) Filed: Nov. 20, 2017

(65) Prior Publication Data

US 2018/0071059 A1 Mar. 15, 2018

Related U.S. Application Data

(63) Continuation of application No. 15/032,680, filed as application No. PCT/US2014/063364 on Oct. 31, 2014, now Pat. No. 9,848,961.

(60) Provisional application No. 61/898,560, filed on Nov. 1, 2013.

(51) Int. Cl.
*A61C 8/00* (2006.01)

(52) U.S. Cl.
CPC .......... *A61C 8/0086* (2013.01); *A61C 8/0054* (2013.01); *A61C 8/0057* (2013.01); *A61C 8/0065* (2013.01); *A61C 8/0068* (2013.01); *A61C 8/0074* (2013.01)

(58) Field of Classification Search
CPC ........... A61C 8/00; A61C 13/08; A61C 13/09; A61C 8/0056; A61C 8/0057; A61C 8/0068; A61C 8/0074; A61C 8/0054
See application file for complete search history.

(56) References Cited

U.S. PATENT DOCUMENTS

| 4,756,689 A * | 7/1988 | Lundgren | ............... A61C 8/005 433/169 |
| 4,881,897 A | 11/1989 | Franek et al. | |
| 4,950,161 A | 8/1990 | Richter | |
| 5,033,962 A | 7/1991 | Scatena | |

(Continued)

FOREIGN PATENT DOCUMENTS

WO 2013/169569 A1 11/2013

OTHER PUBLICATIONS

International Search Report of corresponding International Application No. PCT/US2014/063364 dated Feb. 13, 2015.

*Primary Examiner* — Nicholas Lucchesi
(74) *Attorney, Agent, or Firm* — Bacon & Thomas, PLLC

(57) ABSTRACT

An dental implant has a substantially cylindrical solid base member; an abutment; an implant-abutment junction (IAJ) portion at one end of the base member to retain the abutment to the base member, so that the abutment is able to move within a predetermined distance in an axial direction of the base member, a first cushion adapted to be mounted between the abutment and the base member, and a second cushion, preferably an elastomer, which is sandwiched between the IAJ portion and the abutment, wherein the first and second cushion are able to provide a resistance force when the abutment is pressed to move relatively toward the base member and providing a bouncing back force when the abutment is released from the pressing.

7 Claims, 10 Drawing Sheets

(56) References Cited

U.S. PATENT DOCUMENTS

| | | | |
|---|---|---|---|
| 5,040,982 A | 8/1991 | Stefan-Dogar | |
| 5,368,483 A | 11/1994 | Sutter | |
| 5,556,280 A | 9/1996 | Pelak | |
| 6,315,563 B1 | 11/2001 | Artal | |
| 2003/0224328 A1 | 12/2003 | Sapian | |
| 2006/0024644 A1 | 2/2006 | Cohen | |
| 2007/0005042 A1* | 1/2007 | Anderson | A61C 8/00 604/890.1 |
| 2008/0153063 A1* | 6/2008 | Mullaly | A61C 8/0018 433/174 |
| 2008/0241790 A1* | 10/2008 | Gittleman | A61C 8/0053 433/174 |
| 2008/0261174 A1 | 10/2008 | Gittleman | |
| 2009/0317769 A1 | 12/2009 | Urdaneta | |
| 2010/0304334 A1 | 12/2010 | Layton | |
| 2016/0067016 A1* | 3/2016 | Hur | A61C 8/0089 433/147 |
| 2016/0278909 A1 | 9/2016 | Kelly et al. | |
| 2017/0049393 A1* | 2/2017 | Hyun | A61B 5/157 |

* cited by examiner

US 10,111,735 B2

DOUBLE-CUSHIONED DENTAL IMPLANT

FIELD OF THE INVENTION

The present invention is related to a dental implant, and in particular related to a dental implant with double cushions for absorbing impact force generated during chewing or biting.

BACKGROUND

In natural teeth the periodontal ligament functions as a cushion between tooth and jawbone, absorbing impact force and uniformly transferring occlusal forces to surrounding bone. The distribution of the force depends on micro movement induced by the periodontal ligament. Due to lack of periodontal ligament, dental implant has to directly bond to bone, causing non-uniform stress distribution in bone which might lead to implant failure (Quirynen 1992). Because of the lack of micro movement of implants, most of the force distribution is concentrated at the crest of the ridge. Vertical forces at the bone interface are concentrated at the crestal regions, and lateral forces increase the magnitude of the crestal force distribution.

US 2010/0304334 A1 discloses a dental implant system comprising an implant having a well and an abutment having a post shaped to be received in the tapered well, and in one embodiment shown thereof the implant and the abutment are jointed one to the other with a retentive elastomeric product, enabling an artificial tooth supported by the abutment to move in a fashion similar to that of a natural tooth.

SUMMARY OF THE INVENTION

The inventors of the present application in their previous work (PCT/US2013/039366, filed 3 May 2013) disclose dental implant comprising: a substantially cylindrical hollow base member comprising a wall defining a space in said substantially cylindrical hollow base member, and a plurality of through-thickness holes communicating said space with an outer surface of said wall; an abutment; an implant-abutment junction (IAJ) portion at one end of said base member to retain said abutment to said base member, so that said abutment is able to move within a predetermined distance in an axial direction of said base member; and a first cushion adapted to be mounted between said abutment and said base member for providing a resistance force when said abutment is pressed to move relatively toward said base member and providing a bouncing back force when said abutment is released from said pressing. In one embodiment of the cushioned dental implant, the dental implant further comprises a second cushion which is an elastomer and is sandwiched between said IAJ portion and said abutment. The disclosure of PCT/US2013/039366 is incorporated herein by reference.

When a relatively small/thin dental implant is desired, the previous hollow implant body design may not withstand a large stress/loading. In addition, it will be more difficult to fabricate. Therefore there is a need to design a dental implant comprising a solid implant body with double cushions.

The present invention provides an improved dental implant comprising:
 a solid base member;
 an abutment;
 an implant-abutment junction (IAJ) portion at one end of said base member to retain said abutment to said base member, so that said abutment is able to move within a predetermined distance in an axial direction of said base member;
 a first cushion adapted to be mounted between said abutment and said base member; and
 a second cushion adapted to be sandwiched between said IAJ portion and said abutment,
 wherein the first cushion and the second cushion are two separate members.

Preferably, the first cushion and the second cushion are an elastomer.

Preferably, said abutment comprises a receiving part for receiving a dental prosthesis and a connecting part, wherein said IAJ portion has an axial hole and said connecting part of said abutment has a cylindrical rod portion having a diameter corresponding to said axial hole and an enlarged end extending from said cylindrical rod portion, wherein said cylindrical rod portion is slidably received in said axial hole of said IAJ portion with said enlarged end protruding from one end of said axial hole and another end of said cylindrical rod portion protruding from the other end of said axial hole, wherein said IAJ portion is a separate part and threadedly connected to said one end of said base member, so that the enlarged end of the connecting part of the abutment is prevented from escaping from the axial hole of said IAJ portion, wherein said first cushion is an plane elastomer and is sandwiched between said enlarged end of said connecting part of said abutment and said one end of said base member, and wherein said second cushion is a ring and is mounted on the cylindrical rod portion of said connecting part and sandwiched between said IAJ portion and said receiving part of said abutment.

Preferably, said abutment comprises a receiving part for receiving a dental prosthesis and a connecting part, wherein said IAJ portion has an axial hole and said connecting part of said abutment has a cylindrical rod portion having a diameter corresponding to said axial hole and an enlarged end extending from said cylindrical rod portion, wherein said cylindrical rod portion is slidably received in said axial hole of said IAJ portion with said enlarged end protruding from one end of said axial hole and another end of said cylindrical rod portion protruding from the other end of said axial hole, wherein said IAJ portion is a separate part and connected to said one end of said base member via interference fit connection, so that the enlarged end of the connecting part of the abutment is prevented from escaping from the axial hole of said IAJ portion, wherein said first cushion is an plane elastomer and is sandwiched between said enlarged end of said connecting part of said abutment and said one end of said base member, and wherein said second cushion is a ring and is mounted on the cylindrical rod portion of said connecting part and sandwiched between said IAJ portion and said receiving part of said abutment.

Preferably, said abutment comprises a receiving part for receiving a dental prosthesis and a connecting part having a cylindrical rod portion and an enlarged threaded end extending from said cylindrical rod portion, wherein said IAJ portion has an axial hole having a threaded inner wall portion corresponding to said an enlarged threaded end near an entrance of said axial hole and a smooth inner wall portion following the threaded inner wall portion having a diameter corresponding to that of said enlarged threaded end, wherein said enlarged threaded end is threaded through the threaded inner wall portion and into the smooth inner wall portion of said axial hole, wherein said first cushion is an plane elastomer and is sandwiched between said enlarged end of said connecting part of said abutment and said one end of said base member, and wherein said second cushion is a ring and is mounted on the cylindrical rod portion of said connecting part and sandwiched between said IAJ portion and said receiving part of said abutment.

Preferably, the dental implant of the present invention further comprises a C-shaped or O-shaped buckle, wherein said abutment comprises a receiving part for receiving a dental prosthesis and a connecting part having a cylindrical rod portion and an enlarged end extending from said cylindrical rod portion, wherein said C-shaped or O-shaped buckle is mounted on the cylindrical rod portion and between the enlarged end and the receiving part of said abutment, wherein said IAJ portion has an axial hole having an inner wall portion corresponding to said C-shaped or O-shaped buckle, wherein said C-shaped or O-shaped buckle is elastically detained by the inner wall portion of said axial hole of said IAJ portion, wherein said first cushion is an plane elastomer and is sandwiched between said enlarged end of said connecting part of said abutment and said one end of said base member, and wherein said second cushion is a ring and is mounted on the cylindrical rod portion of said connecting part and sandwiched between said IAJ portion and said receiving part of said abutment.

Preferably, said solid base member comprises a cylindrical body having a sharpened end opposite to said IAJ portion, and said outer surface of said cylindrical body is provided with threads or is smooth.

The first cushion and/or the second cushion are able to provide a resistance force when said abutment is pressed to move relatively toward said base member and providing a bouncing back force when said abutment is released from said pressing. Further, the double-cushioned dental implant in comparison with the single-cushioned dental implant shows a far superiority in a fatigue resistance test.

BRIEF DESCRIPTION OF THE DRAWINGS

FIG. 1b shows a perspective view of elements/parts for assembling the dental implant shown in FIG. 1a.

FIG. 2 shows a perspective view of two parts adapted to be threadably connected to each other for forming an abutment of the dental implant shown in FIG. 1a.

DETAILED DESCRIPTION OF THE INVENTION

Figure 1A:
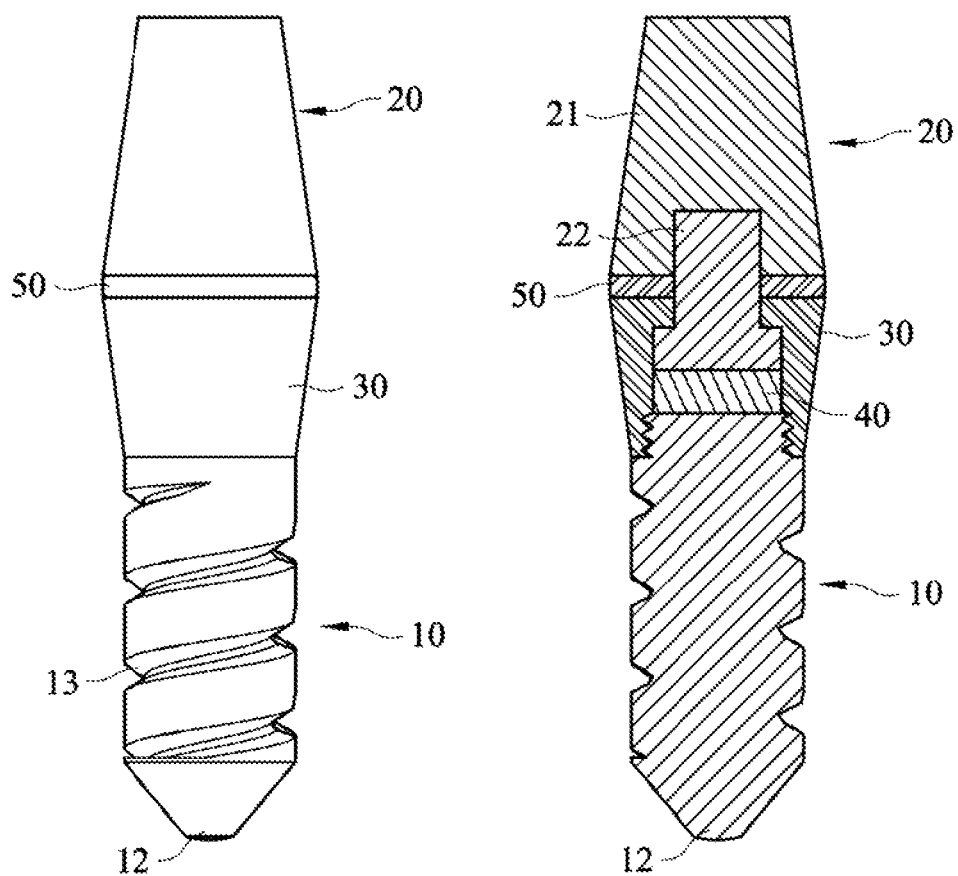
FIG. 1a shows a perspective view and a cross-sectional view of a dental implant constructed according to a first preferred embodiment of the present invention.

Typically a dental implant consists of three major components: fixture, abutment and prosthetic teeth, wherein the fixture is designed to be implanted into jawbone. Abutment serves to support the prosthetic teeth. The prosthetic teeth function as the crown of natural teeth for cutting/grinding foods and transfer bite forces to abutment and fixture.
Features and Advantages of the Present Inventive Dental Implant Design The present inventive dental implant is designed for both one-step/Immediate loading and traditional two-step implantation procedures. The primary features and their respective advantages of the present inventive dental implant design are briefly described in the following:

(1) A dental implant comprising a solid implant body, an abutment, an IAJ, and at least two separate cushions located as indicated in the attached figures.
(2) The abutment comprising a receiving part and a connecting part.
(3) The IAJ is a separate component connecting (by interference fit connection or thread/screw connections) other components and may be dissembled (maintainable) when any component other than the implant body needs to be maintained or replaced.
(4) The IAJ may also comprises a C-shaped buckle (FIG. 7) or O-shaped buckle (FIG. 8), and an axial hole having a diameter so that the C-shaped buckle or the O-shaped buckle is elastically detained in the axial hole.
(5) The implant body surface may be flat or threaded.
(6) The far end of the implant body may be flat or pointed One critical factor leading to dental implant loosening is the non-uniform occlusive force on the root. As mentioned earlier, in natural teeth the periodontal ligament functions as a cushion/buffer between tooth and jawbone, absorbing impact force and uniformly transferring occlusal forces to surrounding bone. Due to lack of periodontal ligament, dental implant has to directly bond to bone, causing non-uniform stress distribution in bone which might lead to implant failure.

Designs incorporating mechanisms able to reduce the negative effects of the non-uniform stress distribution in the alveolar bone include that distributes stresses more uniformly (avoiding stress-concentrated spots) and that absorbing stresses more effectively (simulating the cushion function of periodontal ligament.)

The cushion design of this invention comprises a shock-absorbing elastomer cushion between said IAJ and abutment and as well as between said abutment and said base member. The cushion design simulates the function of periodontal ligament, which reduces the impact effect on the surrounding alveolar bone. The applied occlusion force on abutment can be at least partially transmitted to the cushion.

This shock-absorbing elastomer is preferably made from a polymer-based material, more preferably from a rubber-based material, such as PTFE, PU, PP, etc. This elastomer can effectively absorb the impact (biting) force, thus reducing the negative effect of occlusive force on bone/teeth.

The elastomer cushion may be a single layer, substantially flat, solid, hollow or porous plate, preferably in round shape. The elastomer cushion may also be a multilayer design. The elastomer cushion may also be a one-piece U-shaped (or bowl-shaped three-dimensionally) design.

One primary advantage of these cushion designs is that all the cushions are easily removable, maintainable, and replaceable without damaging or disrupting the implant root or surrounding bone. This replaceable feature is crucial, since the cushion—no matter being made from polymer or metal—is subject to mechanical and/or thermal fatigue, plastic deformation when it is used for an extended period of time.

When a curable or hardenable cushion (for example, a polymer or rubber type cushion prepared from mixing and curing a matrix agent and a hardening agent) is used, the cushion material may be cured (pre-formed) and shaped before being inserted between the IAJ and the abutment (pre-formed). The cushion material may also be cured after being inserted between the IAJ and the abutment, i.e., putting the cushion material in place—between IAJ and abutment—while the cushion material is not fully cured and is still flowable and moldable. One advantage of this in-situ curing method is that the fitness of the cushion between IAJ and abutment is improved and the stress distribution is more effective and uniform.

Examples

Figure 1B:
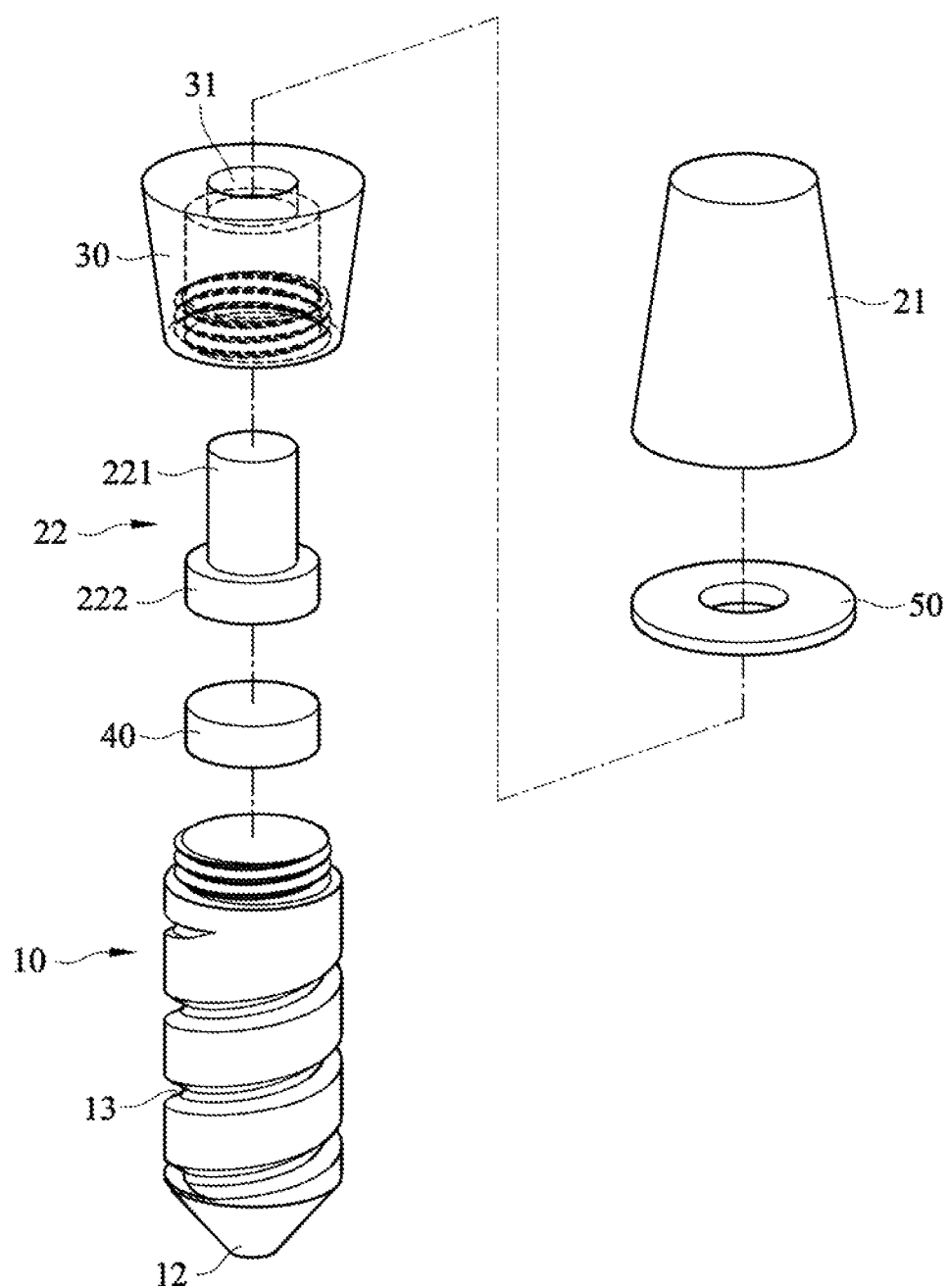

A dental implant constructed according to a first preferred embodiment of the present invention is shown in FIGS. 1a and 1b, which has a substantially cylindrical solid base member 10; an abutment 20; an implant-abutment junction (IAJ) portion 30 at a top end of said base member 10 to retain said abutment 20 to said base member 10, so that said abutment 20 is able to move within a predetermined distance in an axial direction of said base member 10.

Said abutment 20 has a receiving part 21 for receiving a dental prosthesis and a connecting part 22, wherein said IAJ portion 30 has an axial hole 31 and said connecting part 22 of said abutment has a cylindrical rod portion 221 having a diameter corresponding said axial hole 31 and an enlarged end 222 extending from said cylindrical rod portion, wherein said cylindrical rod portion 221 is slidably received in said axial hole 31 of said IAJ portion 30 with said enlarged end 222 protruding from the bottom end of said axial hole 31 and the top end of said cylindrical rod portion protruding from the top end of said axial hole 31. Said IAJ portion 30 is a separate part and threadedly connected to said top end of said base member 10, preventing said abutment 20 from escaping said IAJ portion 30. A first cushion 40 which is a round plate made of elastomer and is put on the top end of the base member 10 before said IAJ portion 30 is threadedly connected to said top end of said base member 10.

The first cushion 40 is sandwiched between said enlarged end 222 of said connecting part 22 of said abutment 20 and the top end of said base member 10 for providing a resistance force when said abutment 20 is pressed to move relatively toward said base member 10 and providing a bouncing back force when said abutment 20 is released from said pressing Said substantially cylindrical solid base member 10 is provided with a sharpened end 12 opposite to said IAJ portion 30, and provided with threads 13 on an outer surface thereof.

Figure 2:
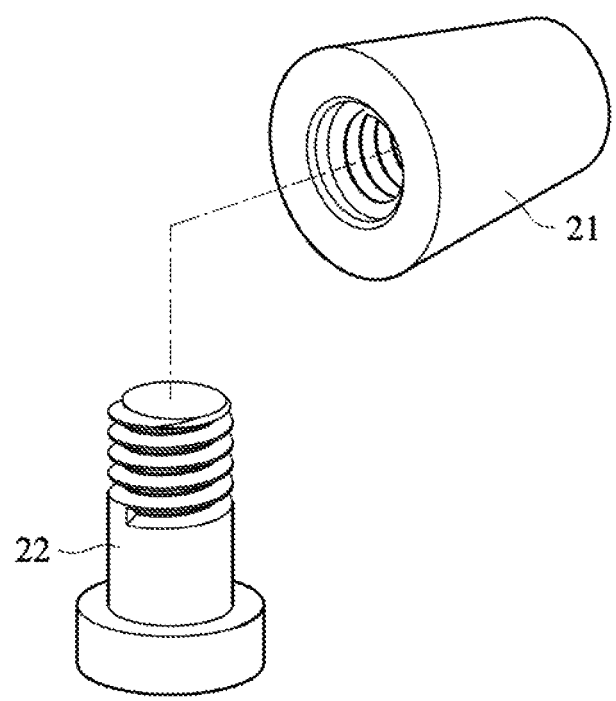

The dental implant further comprises a second cushion 50 which is a ring made of an elastomer, and is mounted on the cylindrical rod portion 221 of said connecting part 22 and is sandwiched between said IAJ portion 30 and said receiving part 21 of said abutment 20. The cylindrical rod portion 221 of said connecting part 22 is plugged into a corresponding recess at a bottom of said receiving part 21 of said abutment 20. Alternatively, said connecting part 22 of said abutment 20 is threadedly connected to said receiving part 21 of said abutment 20 as shown in FIG. 2.

Figure 3:
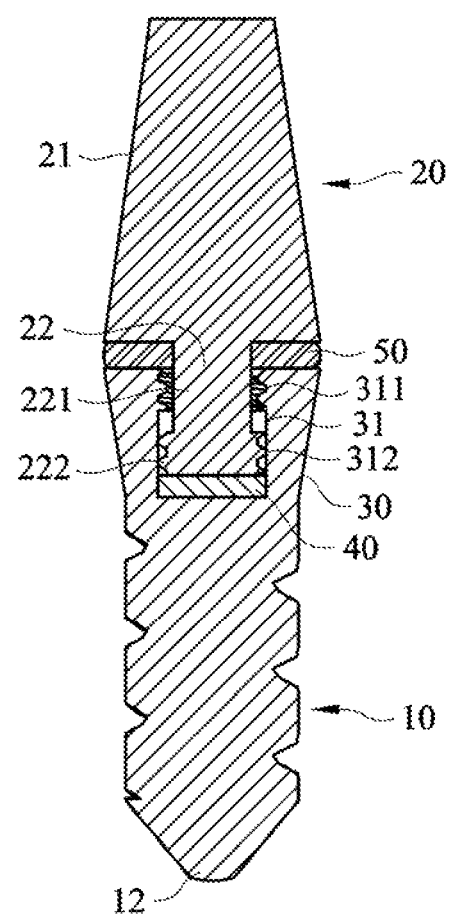
FIG. 3 shows a cross-sectional view of a dental implant constructed according to a second preferred embodiment of the present invention.

A dental implant constructed according to another preferred embodiment of the present invention is shown in FIG. 3, which is similar to the first preferred embodiment shown in FIGS. 1a and 1b except that the abutment 20 and the IAJ portion 30. As shown in FIG. 3, said abutment 20 has a receiving part 21 and a connecting part 22 integrally extending from a bottom of said receiving part 21. The connecting part 22 has a cylindrical rod portion 221 and an enlarged threaded end 222 extending from said cylindrical rod portion 221. The first cushion 40 is mounted similarly to that shown in FIGS. 1a and 1b. The second cushion 50 which is a ring made of an elastomer is mounted on the cylindrical rod portion 221 from the enlarged threaded end 222 of the connecting part 22. The IAJ portion 30 has an axial hole 31 having a threaded inner wall portion 311 corresponding to said an enlarged threaded end 222 and a smooth inner wall portion 312 following the threaded inner wall portion 311 having a diameter slightly larger than that of said enlarged threaded end 222, wherein said enlarged threaded end 222 is threaded through the threaded inner wall portion 311 and into the smooth inner wall portion 312 of said axial hole 31.

Figure 4:
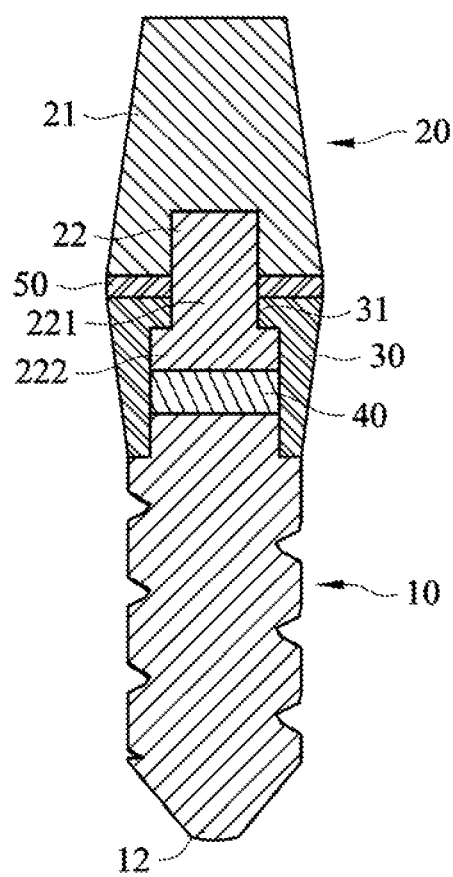
FIG. 4 to 9 show cross-sectional views of dental implants constructed according to other preferred embodiments of the present invention.

Other various changes and modifications to the dental implants described above are shown in FIGS. 4 to 9, wherein like elements or parts are represented by like numerals The dental implant shown in FIG. 4 is similar to the first preferred embodiment shown in FIGS. 1a and 1b except that the IAJ portion 30 is connected to the based member 10 by using an interference fit connection in FIG. 3 instead of threading in FIGS. 1a and 1b.

Figure 5:
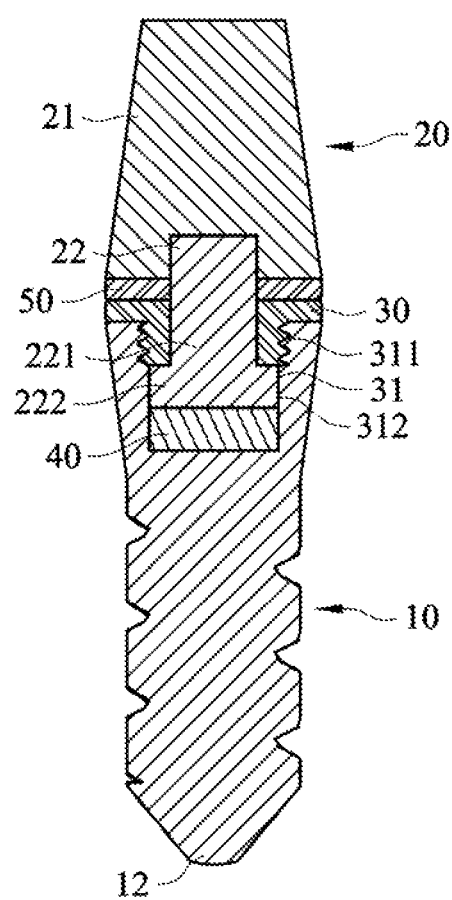

The dental implant shown in FIG. 5 is similar to the first preferred embodiment shown in FIGS. 1a and 1b except the IAJ portion 30. In this embodiment shown in FIG. 5, the IAJ portion 30 is provided with a threaded annular portion, and the base member 10 is provided with an axial hole 31 at a top end thereof. The axial hole 31 has a threaded inner wall portion 311 corresponding to said threaded annular portion and a smooth inner wall portion 312 following the threaded inner wall portion 311 having a diameter slightly larger than that of the enlarged end 222. The IAJ portion 30 is threadedly connected to the top end of the base member 10 through said threaded annular portion of the IAJ portion 30 and the threaded inner wall portion 311 of said axial hole 31. The first cushion 40 and the second cushion 50 are mounted similarly to those shown in FIGS. 1a and 1b.

Figure 6:
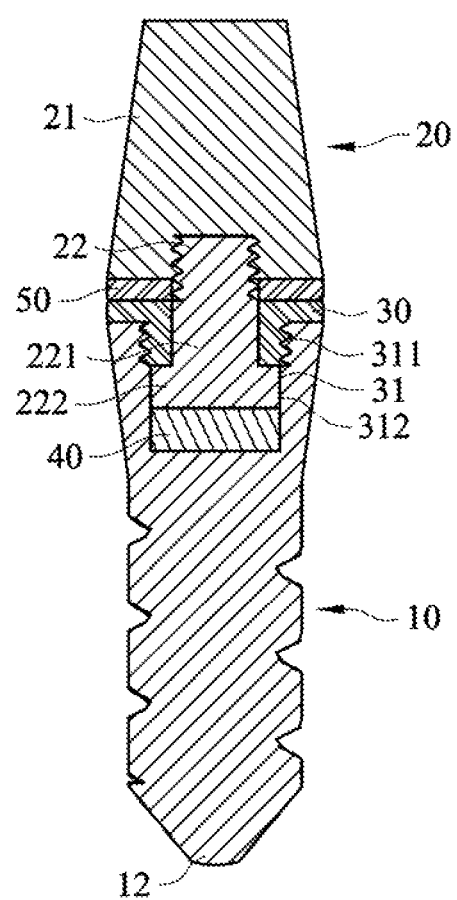

The dental implant shown in FIG. 6 is similar to the embodiment shown in FIG. 5 except that the receiving part 21 is connected to the connecting part 22 of the abutment 20 via threading in FIG. 6 instead of the interference fit connection shown in FIG. 5 or in FIGS. 1a and 1b.

Figure 7:
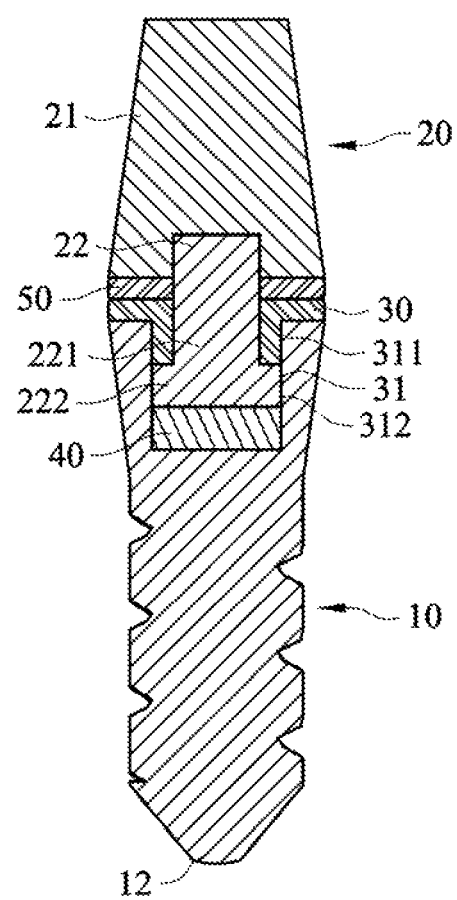

The dental implant shown in FIG. 7 is similar to the embodiment shown in FIG. 5 except that the IAJ portion 30 is connected to the based member 10 by using an interference fit connection in FIG. 7 instead of threading in FIG. 5.

Figure 8:
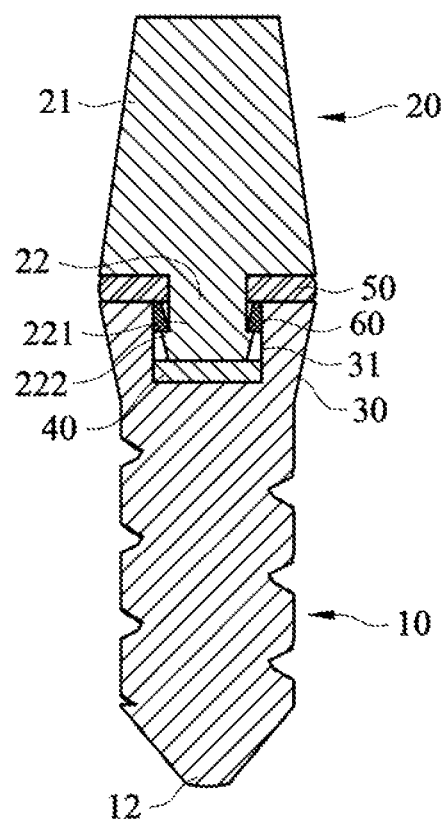

The dental implant shown in FIG. 8 is similar to the embodiment shown in FIG. 3. As shown in FIG. 8, said abutment 20 has a receiving part 21 and a connecting part 22 integrally extending from a bottom of said receiving part 21. The connecting part 22 has a cylindrical rod portion 221 and an enlarged end 222 extending from said cylindrical rod portion 221. The second cushion 50 which is a ring made of an elastomer is mounted on the cylindrical rod portion 221 from the enlarged end 222 of the connecting part 22, and then said connecting part 22 of said abutment 20 is forced to insert into a C-shaped or O-shaped buckle 60, so that said C-shaped or O-shaped buckle 60 is mounted on the cylindrical rod portion 221, and the second cushion 50 is sandwiched between the receiving part 21 and the C-shaped or O-shaped buckle 60. The base member 10 has a sharpened end and a smooth outer surface. The IAJ portion 30 has an axial hole 31 having a diameter slightly smaller than the outer diameter of the C-shaped or O-shaped buckle 60. A first cushion 40 which is a round plate made of an elastomer is placed on a bottom surface of the axial hole 31, and then the abutment 20 together with the second cushion 50 and the C-shaped or O-shaped buckle 60 mounted thereon are forced to insert into the axial hole 31 of the IAJ portion 30 of the base member 10, until the C-shaped or O-shaped buckle 60 is elastically detained by the inner wall portion 321 of the axial hole 31 of said IAJ portion 30, whereby the first cushion 40 is sandwiched between said enlarged end 222 of said connecting part 22 of said abutment 20 and said based member 10, and the second cushion 50 is sandwiched between said IAJ portion 30 of the based member 10 and the receiving part 21 of said abutment 20. The C-shaped or O-shaped buckle 60 is preferably made from a highly elastic material, more preferably from a highly elastic (high modulus) metallic material, so that when the buckle is bent to facilitate installation or removal of the buckle, little plastic (permanent) deformation occurs.

Figure 9:
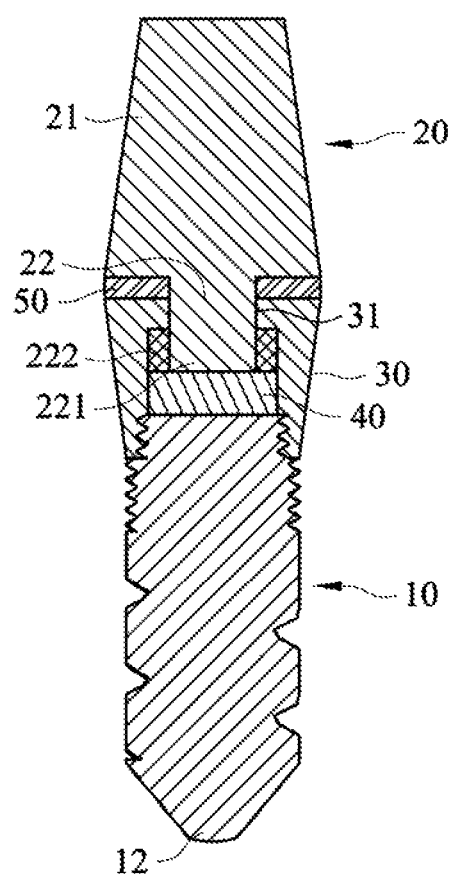

The dental implant shown in FIG. 9 is similar to the embodiment shown in FIGS. 1a and 1b except the abutment 20. As shown in FIG. 9, the connecting part 22 of the abutment 20 has a cylindrical rod portion 221 and a separate enlarged end 222, wherein the separate enlarged end 222 is placed on top of the first cushion 40 before the IAJ portion 30 is threadedly connected to the top end of the base member 10, and then the cylindrical rod portion 221 is inserted into the axial hole 31 of the IAJ portion 30 and is forced to connect to the separate enlarged end 222 via interference fit connection.

Comparison Between Single-Cushioned and Double-Cushioned Designs by Fatigue Testing Method:

A single-cushioned dental implant and a double-cushioned dental implant were manufactured (by a 5-axis precision machining system) from grade-4 commercially pure titanium except the cushions which were hand-made from an elastomeric material (Silagum®, DMG Chemisch-Pharmazeutische Fabrik GmbH, Hamburg, Germany). The double-cushioned dental implant has a construction shown in FIGS. 1a and 1b. The single-cushioned dental implant is the same as the double-cushioned dental implant except that it does not have the second cushion 50.

A servo-hydraulic type testing system (EHF-EG, Shimadzu Co., Tokyo, Japan) was used for the fatigue testing according to the ISO 14801-Dentistry-Implants-Dynamic fatigue test for endosseous dental implants method. 300 N was used as the loading force (F). The load varied sinusoidally between a nominal peak value and 10% of this value. 10 Hz was used as the loading frequency (f). (The specified value of ISO 14801 is no more than 15 Hz) The testing was conducted in air between 20 and 25° C.

Results:

|  | Wave Form | Frequency | Max Load | Min Load | Cycles to failure |
| --- | --- | --- | --- | --- | --- |
| Single cushion | Sin wave | 10 Hz | 300N | 30N | 840 |
| Double cushions | Sin wave | 10 Hz | 300N | 30N | 551340 |

Conclusion

The far superiority of the double-cushioned device to the single-cushioned device in fatigue resistance is clearly demonstrated in this test.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. A dental implant comprising:
    a solid base member;
    an abutment;
    an implant-abutment junction (IAJ) portion at one end of said base member to retain said abutment to said base member, so that said abutment is able to move within a predetermined distance in an axial direction of said base member, wherein said one end of said base member is a flat closed end;
    a first cushion adapted to be sandwiched between said abutment and said flat closed end of said base member only in said axial direction; and
    a second cushion adapted to be sandwiched between said IAJ portion and said abutment,
    wherein the first cushion and the second cushion are two separate members.

2. The dental implant of claim 1, wherein the first cushion and the second cushion are an elastomer.

3. The dental implant of claim 1, wherein said abutment comprises a receiving part for receiving a dental prosthesis and a connecting part, wherein said IAJ portion has an axial hole and said connecting part of said abutment has a cylindrical rod portion having a diameter corresponding to said axial hole and an enlarged end extending from said cylindrical rod portion, wherein said cylindrical rod portion is slidably received in said axial hole of said IAJ portion with said enlarged end protruding from one end of said axial hole and another end of said cylindrical rod portion protruding from the other end of said axial hole, wherein said IAJ portion is a separate part and threadedly connected to said flat closed end of said base member, so that the enlarged end of the connecting part of the abutment is prevented from escaping from the axial hole of said IAJ portion, wherein said first cushion is an plane elastomer and is sandwiched between said enlarged end of said connecting part of said abutment and said flat closed end of said base member, and wherein said second cushion is a ring and is mounted on the cylindrical rod portion of said connecting part and sandwiched between said IAJ portion and said receiving part of said abutment.

4. T The dental implant of claim 3, wherein said solid base member comprises a cylindrical body having a sharpened end opposite to said IAJ portion, and said outer surface of said cylindrical body is provided with threads or is smooth.

5. The dental implant of claim 1, wherein said abutment comprises a receiving part for receiving a dental prosthesis and a connecting part, wherein said IAJ portion has an axial hole and said connecting part of said abutment has a cylindrical rod portion having a diameter corresponding to said axial hole and an enlarged end extending from said cylindrical rod portion, wherein said cylindrical rod portion is slidably received in said axial hole of said IAJ portion with said enlarged end protruding from one end of said axial hole and another end of said cylindrical rod portion protruding from the other end of said axial hole, wherein said IAJ portion is a separate part and connected to said flat closed end of said base member via interference fit connection, so that the enlarged end of the connecting part of the abutment is prevented from escaping from the axial hole of said IAJ portion, wherein said first cushion is an plane elastomer and is sandwiched between said enlarged end of said connecting part of said abutment and said flat closed end of said base member, and wherein said second cushion is a ring and is mounted on the cylindrical rod portion of said connecting part and sandwiched between said IAJ portion and said receiving part of said abutment.

6. T The dental implant of claim 5, wherein said solid base member comprises a cylindrical body having a sharpened end opposite to said IAJ portion, and said outer surface of said cylindrical body is provided with threads or is smooth.

7. T The dental implant of claim 1, wherein said solid base member comprises a cylindrical body having a sharpened end opposite to said IAJ portion, and said outer surface of said cylindrical body is provided with threads or is smooth.

* * * * *